Dec. 12, 1950 E. G. FISHER Plant Pat. 998
ROSE PLANT
Filed Dec. 29, 1949
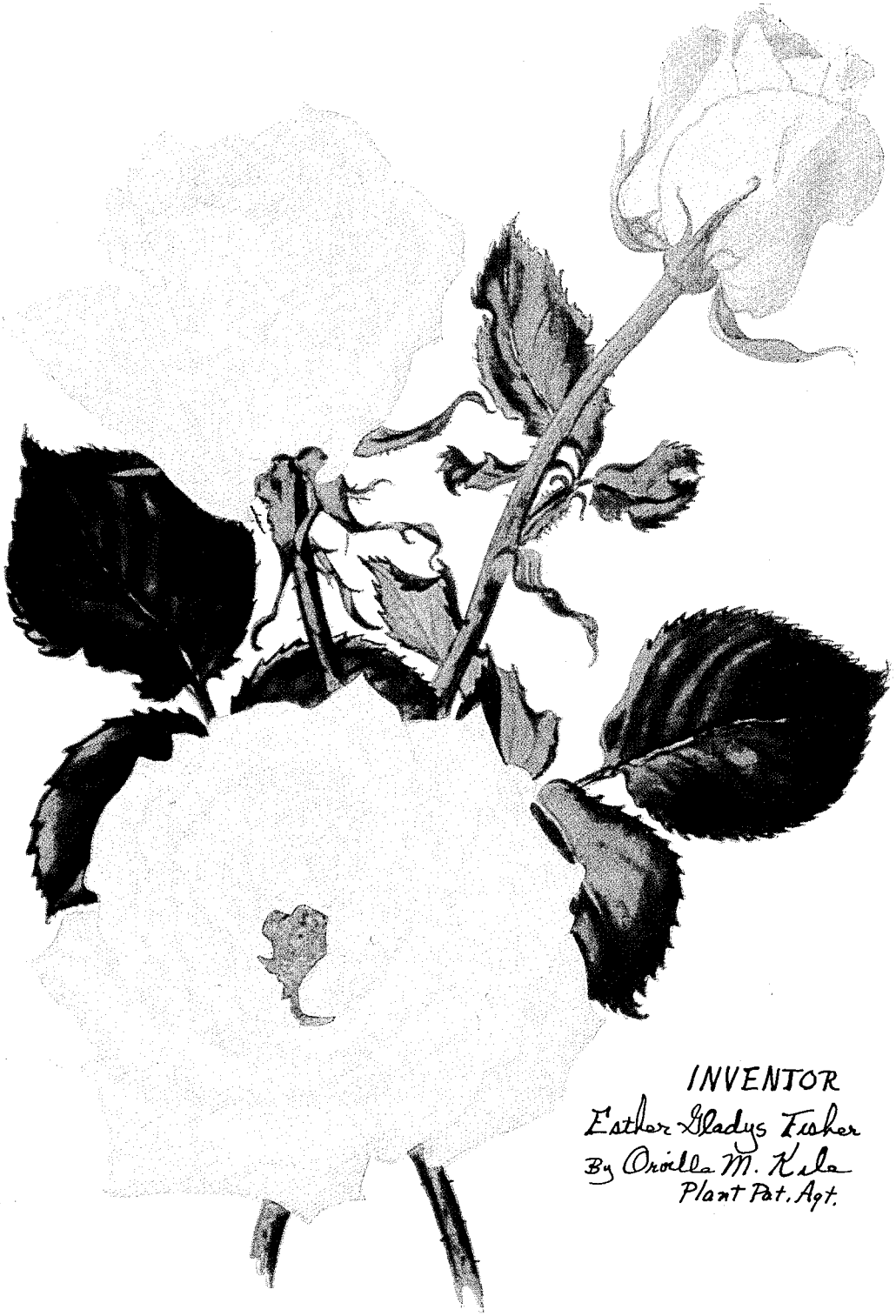
INVENTOR
Esther Gladys Fisher
By Oriella M. Kula
Plant Pat. Agt.

Patented Dec. 12, 1950

Plant Pat. 998

UNITED STATES PATENT OFFICE

998

ROSE PLANT

Esther Gladys Fisher, Woburn, Mass., assignor to
Arnold-Fisher Company, Woburn, Mass.

Application December 29, 1949, Serial No. 135,659

1 Claim. (Cl. 47—61)

My present invention relates to a new and improved variety of hybrid tea rose plant in the outdoor rose class. The variety is the result of a cross made by me in our greenhouses at Woburn, Massachusetts, between the variety Rapture (unpatented) as the female parent and the variety Rome Glory (Plant Patent No. 304) as the male parent. Reproduction by budding has been made at the same location and the variety's outstanding characteristics appear to be permanent.

Outstanding among its characteristics are its vigorous growth and great strength, its hardiness and disease resistance, the strong neck or peduncle, and the form and color of its flower.

The accompanying illustrations show in approximately their true colors, three specimens of the flower of this variety in various stages of opening.

In the following detailed description, color plate numbers refer to Ridgway's Color Standards and Nomenclature. When no plate number is given, the ordinary dictionary meaning of the term is intended.

*The plant*

Type: Outdoor garden variety.

Growth: Exceptionally strong and vigorous—one of the strongest growers known among rose varieties—very much like Radiance (unpatented) in this respect. Has remarkable ability to throw new shoots and long canes. Attains a height of 4 to 5 feet.

Blooming habit: Continuous from early spring to late fall. Has many buds at all times.

Disease resistance: Remarkably free from the usual rose diseases.

Hardiness: More resistant to cold than most rose varieties.

Stems: Very long, sturdy and stiff. Smooth except for a few large thorns. Hellebore Green (Plate XVII), usually with an overlay of brownish red. Although it is primarily an outdoor rose it has the stem qualities of a greenhouse rose. Internodes are short, causing the foliage to be compact. Moderate number of large thorns are irregularly placed along the stem. These are reddish in color, outward-pointing and very sharp.

Foliage:

*Quantity.*—Abundant.

*Leaflets.*—3 to 7.

*Size.*—Medium, terminal leaflet about 2 inches wide by 2½ inches long.

*Shape.*—Very broadly oval with short acuminate apex and rounded base. Serrations are very fine. Central vein is prominent but parallel veinings very slight.

*Texture.*—Leathery.

*Color.*—Unusually dark, tending toward a bluish cast. Empire Green (Plate XXXII) is the nearest in Ridgway's Color Standards and Nomenclature. New shoots are of a reddish color.

*Surface aspect.*—Smooth and waxy on the upper surface; dull on under surface.

*Rachis.*—Heavy; deeply grooved and red-tinged on upper side; smooth on under side and same color as leaf.

*Stipules.*—Usually very small; clinging.

*The flower*

Bud:

*Shape.*—Small, but broad at the base. Cone-shaped when small. Upon opening farther, it becomes long and pointed.

*Size.*—Open bud is approximately 1¾ inches long.

*Color.*—Approximately Deep Rose Pink (Plate XXII), shaded a little darker at the edges of the petals.

*Opening.*—Slow and even. Not affected by adverse weather conditions.

*Peduncle.*—Strong, wiry, relatively short, and usually largely overlaid with red.

*Calyx.*—Encloses most of ovary. Sepal lobes not completely divided.

*Sepals.* — Mostly simple. Do not reflex against stem but curve gracefully about base of flower.

Flower:

*Borne.*—Singly on long, sturdy stems.

*Size.*—Large, measuring up to 5 inches across when grown in the open.

*Form.*—High-centered to globular, which form is retained. Stamens are seldom visible in the open flower but in some cases display stamens as indicated in the illustrations. As the flower open, the petals roll backward very slightly at the edges, sometimes forming a slight pointed effect.

*Color.*—The color varies in the different seasons but in the autumn season is approximately Deep Rose Pink (Plate XII) in the depths of the rose and somewhat lighter on the edges, the entire flower lightening as it ages. The color of the rose is a little lighter at some seasons of the year, but always it is in the range of pink to rose pink.

*Fragrance.*—Mild, fruity fragrance.
*Petalage.*—22 to 33 petals.
*Longevity.*—Keeps excellently both on the bush and as a cut flower.

Petals:
*Shape.*—Slightly obcordate.
*Aspect.*—Smooth.
*Texture.*—Very substantial.
*Size.*—Outer petals average 2½ inches by 2¾ inches.
*Color.*—Approximately Deep Rose Pink (Plate XII), which is pretty evenly spread over both surfaces except for the creamy aiglet.
*Persistence.*—Cling until dead.
*Arrangement.*—Formal.

Reproductive organs:
*Pistils.*—A very large number. Short but set upon a high, pithy mound. *Styles* white with red tip. *Stigmas* light yellow.
*Stamens.*—Surround pistils. Attached well under the edge of pistils and curved so as to encase them. Less numerous than pistils. *Filaments* red. *Anthers* yellow.

In a great many specimens there are small bud-like formations mixed with the stamens surrounding the pistils. In some cases these formations entirely surround the pistils. The presence of these formations makes for a very large center.
*Ovary.*—Mostly enclosed in the calyx, very little extending below the calyx and visible.

Having thus disclosed by invention, I claim:

The new and distinct variety of hybrid tea rose plant, substantially as herein shown and described, characterized particularly by its adaptability to garden culture, its exceedingly great strength and vigor of growth; its relative hardiness and disease resistance; its long, sturdy canes and flower stems; the strong, wiry neck or peduncle of the flower; and the high-centered form and rose pink color of its flower, which lasts unusually well.

ESTHER GLADYS FISHER.

No references cited.